(12) United States Patent
Sung et al.

(10) Patent No.: US 7,348,026 B2
(45) Date of Patent: Mar. 25, 2008

(54) NANOPARTICLES FOR TARGETING HEPATOMA CELLS

(76) Inventors: Hsing-Wen Sung, 7F, No. 15, Alley 7, Lane 298, Section 2, Kung Fu Road, Hsinchu (TW) 300; Hsiang-Fa Liang, 1F., No. 1, Lane 400, Jhongjheng Rd., Shindian City, Taipei (TW) 23148; Ting-Fan Yang, 4F, No. 1, Lane 161, Sec. 4, Jhongshan E. Rd., Jhongli City, Taoyuan County 330 (TW); Chin-Tsung Huang, No. 87, Chin-Hu Rd., Su-Ao City (TW) 270; Hosheng Tu, 15 Riez, Newport Beach, CA (US) 92657

( * ) Notice: Subject to any disclaimer, the term of this patent is extended or adjusted under 35 U.S.C. 154(b) by 511 days.

(21) Appl. No.: 10/958,864

(22) Filed: Oct. 5, 2004

(65) Prior Publication Data

US 2006/0073209 A1    Apr. 6, 2006

(51) Int. Cl.
- *A61K 9/58* (2006.01)
- *A61K 9/14* (2006.01)
- *A61K 9/16* (2006.01)

(52) U.S. Cl. ............... 424/458; 424/489; 424/491
(58) Field of Classification Search ............ 424/458, 424/489, 491
See application file for complete search history.

(56) References Cited

U.S. PATENT DOCUMENTS

| | | |
|---|---|---|
| 6,177,274 B1 | 1/2001 | Park et al. |
| 6,623,729 B2 | 9/2003 | Park et al. |
| 6,752,981 B1 | 6/2004 | Erion et al. |

OTHER PUBLICATIONS

C. Li, Adv. Drug Deliver. Rev. 54 (2002) 695-713.
K. Na, K.H. Park, S.W. Kim, Y.H. Bae, J. Control. Release 69 (2000) 225-236.
J.M. Saul, A. Annapragada, J.V. Natarajan, R.V. Bellamkonda, J. Control. Release 92 (2003) 49-67.
H.C. Liang, W.H. Chang, K.J. Lin, H.W. Sung, J. Biomed. Mater. Res. 65A (2003) 271-282.
K. Na, T.B. Lee, K.H. Park, E.K. Shin, Y.B. Lee, H.K. Choi, Eur. J. Pharm. Sci. 18 (2003) 165-173.
Y.S. Nam, H.S. Kang, J.Y. Park, T.G. Park, S.H. Han, I.S. Chang, Biomaterials 24 (2003) 2053-2059.
Y. Matsumura, H. Maeda, Cancer Res. 46 (1986) 6387-6392.
M. Hashida, K. Akamatsu, M. Nishikawa, F. Yamashita, Y. Takakura, J. Control. Release (1999) 253-262.
J.H. Han, Y.K. Oh, D.S. Kim, C.K. Kim, Int. J. Pharm. 188 (1999) 39-47.
R.J. Fallon, A.L. Schwartz, Adv. Drug Deliver. Rev. 4 (1989) 49-63.
J. Lee, E.C. Cho, K. Cho, J. Control. Release 94 (2004) 323-335.
A. Richard, A. Margaritis, Crit. Rev. Biotechnol. 21 (2001) 219-232.
C. Li, D.F. Yu, A. Newman, F. Cabral, C. Stephens, N. Hunter, L. Milas, S. Wallace, Cancer Res. 58 (1998) 2404-2409.
S.H. Yoon, J.H. Do, S.Y. Lee, H.N. Chang, Biotechnol. Lett. 22 (2000) 585-588.
F.A. Troy, J. Biol. Chem. 248 (1973) 316-324.
W.N.E. van Dijk-Wolthuis, S.K.Y. Tsang, J.J. Kettenes-van den Bosch, W.E. Hennink, Polymer 38 (1997) 6235-6242.
R. Gref, M. Lück, P. Quellec, M. Marchand, E. Dellacherie, S. Harnisch, T. Blunk, R.H. Müller, Colloid. Surface. B, 18 (2000) 301-313.
M. Chacón, J. Molpeceres, L. Berges, M. Guzmán, M.R. Aberturas, Eur. J. Pharm. Sci. 8 (1999) 99-107.
A.V. Kabanov, I.R. Nazarova, I.V. Astafieva, E.V. Batrakova, V.Y. Alakhov, A.A. Yaroslavov, V.A. Kabanov, Macromolecules 28 (1995) 2303-2314.
E.S. Lee, H.J. Shin, K. Na, Y.H. Bae, J. Control. Release 90 (2003) 363-374.
H.W. Sung, W.H. Chang, C.Y. Ma, M.H. Lee, J. Biomed. Mat. Res. 64A (2003) 427-438.
H.C. Liang, W.H. Chang, H.F. Liang, M.H. Lee, H.W. Sung, J. Appl. Polym. Sci. 91 (2004) 4017-4026.
A. David, P. Kopeckova, A. Rubinstein, J. Kopeccek, Bioconj. Chem. 12 (2001) 890-899.
C.N. Chen, H.W. Sung, H.F. Liang, W.H. Chang, J. Biomed Mater. Res. 61 (2002) 360-369.
G.A. Birrer, A. Cromwick, R.A. Gross, Int. J. Biol. Macromol. 16 (1994) 265-275.
A. Goto, M. Kunioka, Biosci. Biotechnol. Biochem. 56 (1992) 1031-1035.
I.L. Shih, Y.T. Van, Bioresource Technol. 79 (2001) 207-225.
C.O. Beauchamp, S.L. Gonias, D.P. Menapace, S.V. Pizzo, Anal. Biochem. 131 (1983) 25-33.
Y. Dong, S.S. Feng, Biomaterials 25 (2004) 2843-2849.
M. Hashida, S. Takemura, N. Nishikawa, Y. Takakura, J. Control. Release 53 (1998) 301-310.
D.C. Litzinger, A.M.J. Buiting, N. Rooijen, L. Huang, Biochim. Biophys. Acta, 1190 (1994) 99-107.
H. Maeda, Y. Matsumura, Crit. Rev. Ther. Drug Carrier Syst. 6 (1989) 193-210.

*Primary Examiner*—Maryam Monshipouri (57) ABSTRACT

The invention discloses the nanoparticles composed of γ-PGA-PLA block copolymers conjugated with galactosamine as a potential drug delivery system for treating liver cancers.

18 Claims, 9 Drawing Sheets

PLA          γ-PGA (b)

NANOPARTICLES FOR TARGETING HEPATOMA CELLS

FIELD OF THE INVENTION

The present invention is related to medical uses of nanoparticles composed of poly(γ-glutamic acid)-poly(lactide) block copolymers and their uptake by HepG2 cells.

BACKGROUND OF THE INVENTION

Chemotherapy for cancers is usually limited by the toxicity of drugs to normal tissues. Additionally, short circulation half-life in plasma, limited aqueous solubility, and non-selectivity are usually encountered by most of the currently available anticancer drugs and thus restrict their therapeutic efficacy (Adv. Drug Deliver. Rev. 2002; 54:695-713). To reduce the toxicity and increase the therapeutic efficacy of anticancer drugs, various drug carriers, such as soluble polymers, polymeric nanoparticles, liposomes, and microspheres have been investigated (J. Control. Release 2000; 69:225-236; J. Control. Release 2003; 92:49-67; J. Biomed. Mater. Res. 2003; 65A:271-282). The biomedical and pharmaceutical applications of self-assembled nanoparticles have recently attracted extensive attentions (Eur. J. Pharm. Sci. 2003; 18:165-173). The self-assembled nanoparticles are composed of a hydrophobic inner core and a hydrophilic outer shell. Core-forming hydrophobic block may affect the drug loading capacity and its release kinetics as a result of hydrophobic interactions between drugs and polymers. In contrast, the hydrophilic shell-forming block determines surface properties of the nanoparticles and influences interactions between the surrounding environments and the nanoparticles (Biomaterials 2003; 24:2053-2059).

Nanoparticles may be delivered to specific sites by size-dependant passive targeting or by active targeting (Cancer Res. 1986; 46:6387-6392; J. Control. Release 1999; 253-262). To obtain a high degree of selectivity to a specific organ and to enhance the uptake of drug-loaded nanoparticles into the target cells, active targeting has been attempted by many investigators. Liver has been one of the most desirable target organs in the body due to various liver-related metabolic and infectious diseases and cancers (Int. J. Pharm. 1999; 188:39-47). The asialoglycoprotein (ASGP) receptor is known to be present on hepatocytes and several human hepatoma cell lines (Adv. Drug Deliver. Rev. 1989; 4:49-63). Therefore, liver targeting may be achieved by designing drug delivery systems conjugated with a ligand that can bind to the ASGP receptors.

Poly(lactide) (PLA), poly(ε-caprolactone) (PCL), poly(β-benzyl L-aspartate) (PLBA), and poly(γ-benzyl L-glutamate) (PLBG) have been used mostly for the core-forming hydrophobic segment of nanoparticles (J. Control. Release 2004; 94:323-335). On the other hand, poly(ethylene oxide) (PEO), a non-toxic and highly hydrated polymer, has been used as the outer shell segment of nanoparticles because of its superior biocompatibility (J. Control. Release 2004; 94323-335). In the present invention, PLA was used for the hydrophobic segment of the block copolymer, while a natural compound [poly(γ-glutamic acid), γ-PGA], produced as capsular substance or as slime by members of the genus *Bacillus*, was used as the hydrophilic segment (Crit. Rev. Biotechnol. 2001; 21219-232).

γ-PGA is unique in that it is composed of naturally occurring L-glutamic acid linked together through amide bonds rather than a nondegradable C—C backbone such as PEO. It was reported that this naturally occurring γ-PGA is a water-soluble, biodegradable, and non-toxic polymer (Crit. Rev. Biotechnol. 2001; 21219-232). A related, but structurally different, polymer poly(α-glutamic acid), (α-PGA) is usually synthesized from poly(γ-benzyl-L-glutamate) by removing the benzyl protecting group with the use of hydrogen bromide (Adv. Drug Deliver. Rev. 2002; 54:695-713). Li et al. conjugated paclitaxel onto α-PGA via covalent bonding to form a new drug formulation (Cancer Res. 1998; 58:2404-2409). Their pre-clinical data suggested that the uptake of α-PGA-paclitaxel by tumor cells was about 5-fold greater than that of paclitaxel. Additionally, α-PGA-paclitaxel had a significantly longer circulation half-life in plasma than paclitaxel (Adv. Drug Deliver. Rev. 2002; 54:695-713).

Some aspects of the invention relate to developing novel self-assembled nanoparticles composed of γ-PGA-PLA block copolymers. Physicochemical characteristics of the prepared nanoparticles are examined by dynamic light scattering, transmission electron microscopy, atomic force microscopy, and fluorescence spectroscopy. For the potential of targeting liver cancer cells, the prepared nanoparticles are further conjugated with galactosamine. Hashida et al. reported using α-PGA as a polymeric backbone and galactose moiety as a ligand to target hepatocytes (J. Control. Release 1999; 253-262). Their in vivo results indicated that the galactosylated α-PGA had a remarkable targeting ability to hepatocytes and degradation of α-PGA was observed in the liver. The internalization efficiency of the prepared nanoparticles with or without galactosamine conjugated into HepG2 cells (a liver cancer cell line) was examined in vitro using a confocal laser scanning microscope.

There is, therefore, a clinical need for providing nanoparticles composed of γ-PGA-PLA block copolymers conjugated with galactosamine as a potential drug delivery system for the treatment of liver cancers.

SUMMARY OF THE INVENTION

Some aspects of the invention relate to a process for preparing self-assembled nanoparticles using poly(γ-glutamic acid) (γ-PGA) and poly(lactide) (PLA) to synthesize block copolymers via a simple coupling reaction between γ-PGA and PLA. In a further embodiment for targeting liver cancer cells, galactosamine is further conjugated on the prepared nanoparticles as a targeting moiety. γ-PGA, a water-soluble, biodegradable, and non-toxic compound, was produced by microbial fermentation (*B. licheniformis*, ATCC 9945a) and then was hydrolyzed. The hydrolyzed γ-PGA with a molecular weight of 4 kDa and a polydispersity of 1.3 was used, together with PLA (10 kDa, polydispersity 1.1), to synthesize block copolymers. The prepared nanoparticles had a mean particle size of about 140 nm with a zeta potential of about −20 mV.

The results obtained by the TEM and AFM examinations show that the morphology of the prepared nanoparticles is spherical in shape with a smooth surface. In the stability study, no aggregation or precipitation of nanoparticles was observed during storage for up to 1 month, as a result of the electrostatic repulsion between the negatively charged nanoparticles. With increasing the galactosamine content conjugated on the rhodamine-123-containing nanoparticles, the intensity of fluorescence observed in HepG2 cells increased significantly. Additionally, the intensity of fluorescence observed in HepG2 cells incubated with the nanoparticles with or without galactosamine conjugated increased approximately linearly with increasing the duration of incubation. In contrast, there was no fluorescence observed in Hs68 cells (without ASGP receptors) incubated with the nanoparticles with galactosamine conjugated. The aforementioned results indicated that the galactosylated nanoparticles prepared in the study had a specific interaction with HepG2 cells via ligand-receptor recognition.

Some aspects of the invention relate to a method of treating liver cancers in a patient comprising administering a therapeutically effective amount of nanoparticles composed of γ-PGA-PLA block copolymers conjugated with galactosamine. In one embodiment, the nanoparticles comprise a hydrophobic inner core and a hydrophilic outer shell. In another embodiment, the nanoparticles comprise a hydrophilic inner core and a hydrophobic outer shell.

In a further embodiment, the effective amount of nanoparticles is a particle concentration of up to 100 μg/ml. In some embodiment, the γ-PGA component prior to polymerization has a molecular weight of about 4 kDa with a polydispersity of about 1.3.

In some embodiment, the mean particle size for nanoparticles is in the range of about 50 to 400 nm, preferably in the range of about 100 to 200 nm, and more preferably in the range of about 100 to 150 nm.

Some aspects of the invention relate to a method of treating liver cancers in a patient comprising administering a therapeutically effective amount of nanoparticles composed of γ-PGA-PLA block copolymers conjugated with galactosamine, wherein the nanoparticles are loaded with at least a pharmaceutically active compound or an anticancer drug. In a further embodiment, the pharmaceutically active compound is selected from the group consisting of doxorubicin, adriamycin, cisplatin, taxol, 5-fluorouracil, and combination thereof. In a further embodiment, the pharmaceutically active compound is selected from the group consisting of epipodophyllotoxins, camptothecins, endiyne antibiotics, taxanes, coformycins, anthracycline glycosides, mytomycin, combretastatin, anthrapyrazoles, polyamine biosynthesis inhibitors, and combination thereof.

Some aspects of the invention relate to a compound for treating liver cancers in a patient comprising a therapeutically effective amount of nanoparticles composed of γ-PGA-PLA block copolymers conjugated with galactosamine.

BRIEF DESCRIPTION OF THE DRAWINGS

Additional objects and features of the present invention will become more apparent and the disclosure itself will be best understood from the following Detailed Description of the Exemplary Embodiments, when read with reference to the accompanying drawings.

DETAILED DESCRIPTION OF THE EXEMPLARY EMBODIMENTS

The preferred embodiments of the present invention described below relate particularly to a preparation of nanoparticles composed of poly(γ-glutamic acid)-poly(lactide) block copolymers and evaluation of their uptake by HepG2 cells. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

Over the past few decades, biodegradable nanoparticles composed of amphiphilic block copolymers have attracted considerable interests as an effective drug carrier. Additionally, numerous attempts have been made to increase the effectiveness of anticancer drugs by increasing their concentration at the target site. In this study, biodegradable and biocompatible polymers, γ-PGA and PLA, were used to synthesize γ-PGA-PLA block copolymers via a simple coupling reaction between γ-PGA and PLA to prepare self-assembled nanoparticles. Also, galactosamine was conjugated on the prepared nanoparticles as a targeting moiety.

γ-PGA is a naturally occurring anionic homo-polyamide that is made of L-glutamic acid units connected by amide linkages between α-amino and γ-carboxylic acid groups (Crit. Rev. Biotechnol. 2001; 21:219-232). It is in exocellular polymer of certain *Bacillus* species that is produced within cells via the TCA cycle and is freely excreted into the fermentation broth. Its exact biological role is not fully known, although it is likely that γ-PGA is linked to increasing the survival of producing strains when exposed to environmental stresses. Because of its water-solubility, biodegradability, edibility, and non-toxicity toward humans and the environment, several applications of γ-PGA in food, cosmetics, medicine, and water treatment have been investigated in the past few years.

EXAMPLE NO. 1

Materials and Methods of Nanoparticles Preparation

PLA is herein an abbreviated term representing poly(L-lactide), Mn at 10 kDa, with a polydispersity of 1.1 determined by the GPC analysis. Dimethyl sulfoxide (DMSO<0.01% water), N,N'-carbonyldiimidazole (CDI, 98%), and dichloromethane were obtained from Fluka (Buchs, Switzerland). L-glutamic acid (>99%), N-(3-dimethylaminopropyl)-N'-ethylcarbodiimide (EDC), N-hydroxysuccinimide (NHS), galactosamine, hydrophobic dye rhodamine-123, and sodium cholate were purchased from Sigma, USA. Pyrene as a fluorescence probe was acquired from Aldrich, USA. 4-Dimethylaminopyridine (DMAP) and 1,4-dioxane were purchased from ACROS (Janssen Pharmaceuticalaan, Belgium). All other chemicals used were reagent grade.

EXAMPLE NO. 2

Production and Purification of γ-PGA

γ-PGA (FIG. 1) was produced by *Bacillus licheniformis* (ATCC 9945, Bioresources Collection and Research Center, Hsinchu, Taiwan) as per the method reported by Yoon et al. with slight modifications (Biotechnol. Lett. 2000; 22:585-588). Highly mucoid colonies (ATCC 9945a) were selected from *Bacillus licheniformis* (ATCC 9945) cultured on the E medium (L-glutamic acid, 20.0 g/l; citric acid, 12.0 g/l; glycerol, 80.0 g/l; $NH_4Cl$, 7.0 g/l; $K_2HPO_4$, 0.5 gl; $MgSO_4.7H_2O$, 0.5 g/l; $FeCl_3.6H_2O$, 0.04 g/l; $CaCl_2.2H_2O$, 0.15 g/l; $MnSO_4.H_2O$, 0.104 g/l, pH 6.5) agar plates at 37° C. for several times. Subsequently, young mucoid colonies were transferred into 10 ml E medium and grown at 37° C. in a shaking incubator at 250 rpm for 24 hours. Afterward, 500 μl of culture broth was mixed with 50 ml E medium and was transferred into a 2.5-1 jar-fermentor (KMJ-2B, Mituwa Co., Osaka, Japan) containing 950 ml of E medium. Cells were cultured at 37° C. The pH was controlled at 6.5 by automatic feeding of 25% (v/v) $NH_4OH$ and 2M HCl. The dissolved oxygen concentration (DOC) was initially controlled at 40% of air saturation by supplying air and by controlling the agitation speed up to 1000 rpm.

After 40 hours, cells were separated from the culture broth by centrifugation for 20 minutes at 12000×g at 4° C. The supernatant containing γ-PGA was poured into 4 volumes of methanol and left overnight with gentile stirring. The resulting precipitate containing crude γ-PGA was collected by centrifugation for 40 minutes at 12000×g at 4° C. and then was dissolved in distilled water to remove insoluble impurities by centrifugation for 20 minutes at 24000×g at 4° C. The aqueous γ-PGA solution was desalted by dialysis (MWCO: 12000-14000, Spectrum Laboratories, Inc., Laguna Hills, Calif.) against distilled water for 12 hours with water exchanges several times, and finally was lyophilized to obtain pure γ-PGA.

The purified γ-PGA was confirmed by the proton nuclear magnetic resonance ($^1$H-NMR) and the Fourier transformed infrared (FT-IR) analyses. Analysis of $^1$H-NMR was conducted on a NMR spectrometer (Varian Unityionva 500 NMR Spectrometer, MO) using DMSO-$d_6$ at 2.49 ppm as an internal reference. Test samples used for the FT-IR analysis first were dried and ground into a powder form. The powder then was mixed with KBr (1:100) and pressed into a disk. Analysis was performed on an FT-IR spectrometer (Perkin Elmer Spectrum RX1 FT-IR System, Buckinghamshire, England). The samples were scanned in the range of 400-4000 $cm^{-1}$.

Figure 2:
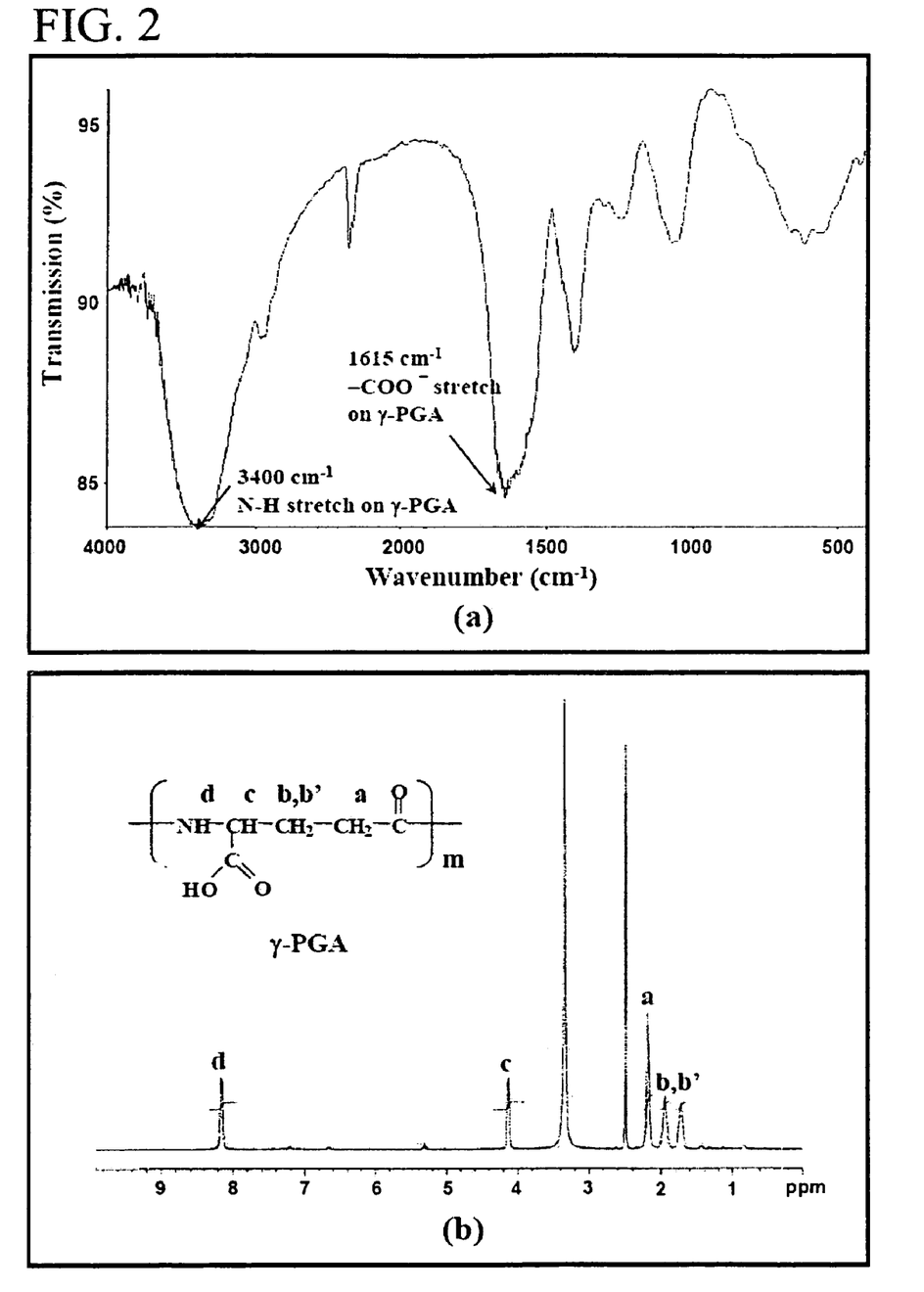
FIG. 2 shows (a) FT-IR and (b) $^1$H-NMR spectra of the purified γ-PGA obtained by microbial fermentation.

FIG. 2a and FIG. 2b show the FT-IR and $^1$H-NMR spectra of the purified γ-PGA obtained from fermentation, respectively. As shown in the FT-IR spectrum (FIG. 2a), a characteristic band at 1615 $cm^{-1}$ for the associated carboxylic acid salt (—$COO^-$ antisymmetric stretch) on γ-PGA was observed. The characteristic absorption due to the C=O in secondary amides (amide I band) was overlapped with the characteristic band of —COO. Additionally, the characteristic peak observed at 3400 $cm^{-1}$ was the N—H stretch of γ-PGA. In the $^1$H-NMR spectrum, five chief signals observed at 1.73, 1.94, 2.19, 4.14, and 8.15 ppm represent the protons of β-$CH_2$, γ-$CH_2$, α-CH, and amide, respectively. These results indicated that the observed FT-IR and $^1$H-NMR spectra correspond well to those expected for γ-PGA. Additionally, the fermented product after purification showed no detected macromolecular impurities by the $^1$H-NMR analysis, suggesting that the obtained white power of γ-PGA is highly pure. It was reported that *Bacillus licheniformis* 9945a does not produce extracellular polysaccharide products (Int. J. Biol. Macromol. 1994; 16:265-275).

EXAMPLE NO. 3

Hydrolysis and Analysis of γ-PGA

The average molecular weight (Mn) of the purified γ-PGA obtained via the previous procedure in Example No. 2 was about 320 kDa. The purified γ-PGA was then hydrolyzed in a tightly sealed steel container at 150° C. for distinct durations (J. Biol. Chem. 1973; 248:316-324). The average molecular weight along with the polydispersity of the hydrolyzed γ-PGA were determined by a gel permeation chromatography (GPC) system equipped with a series of PL aquagel-OH columns (one Guard 8 μm, 50×7.5 mm and two MIXED 8 μm, 300×7.5 mm, PL Laboratories, UK) and a refractive index (RI) detector (RI2000-F, SFD, Torrance, Calif.). Polyethylene glycol (molecular weights of 106-22,000) and polyethylene oxide (molecular weights of 20,000-1,000,000) standards of narrow polydispersity (PL Laboratories, UK) were used to construct a calibration curve. The mobile phase contained 0.01M $NaH_2PO_4$ and 0.2M $NaNO_3$ and was brought to a pH of 7.0. The flow rate of mobile phase was 1.0 ml/min, and the columns and the RI detector cell were maintained at 30° C.

Figure 3:
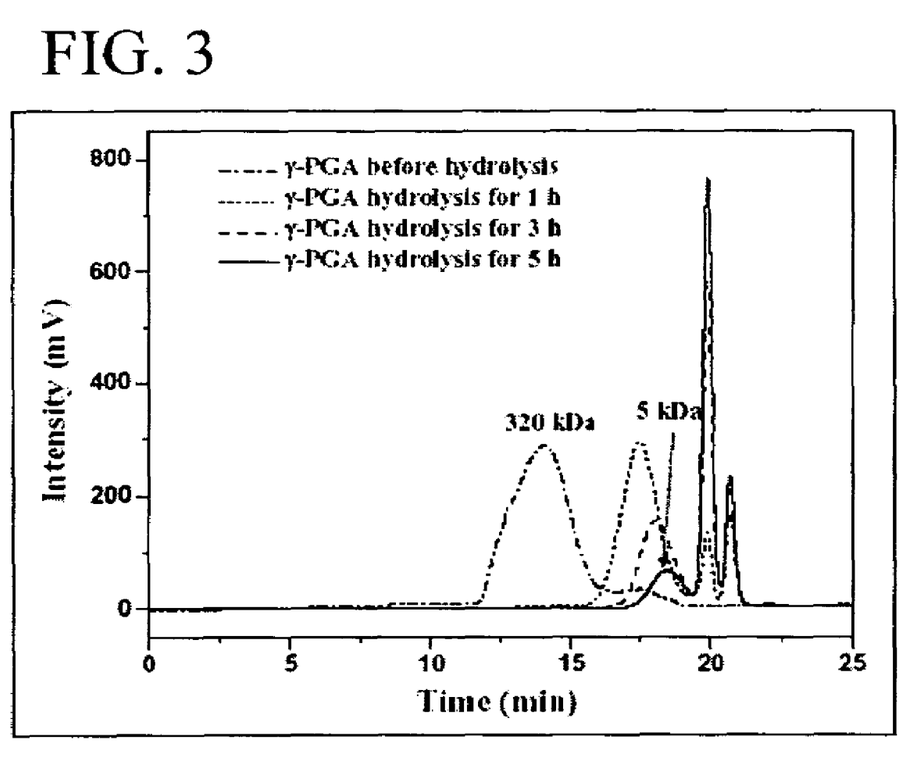
FIG. 3 shows chromatogram of the hydrolyzed γ-PGA obtained in aqueous solution at 150° C. for distinct durations.

In the example, low-molecular-weight γ-PGA was produced by hydrolyzing the purified γ-PGA obtained from fermentation at 150° C. for distinct durations. Hydrolysis of γ-PGA in aqueous solution at different temperatures was proposed as a method to fragment γ-PGA (Biosci. Biotechnol. Biochem. 1992; 56:1031-1035). Solutions of the purified γ-PGA obtained from fermentation and the hydrolyzed γ-PGA were analyzed by a GPC system. As shown in FIG. 3, the purified γ-PGA obtained from fermentation had a high molecular weight (Mn ~320 kDa) with a polydispersity of about 1.8. In the hydrolysis of the purified γ-PGA, it was found that the longer duration the hydrolysis, the lower molecular weight of γ-PGA was produced. When γ-PGA was hydrolyzed at 150° C. for 5 hours, the molecular weight of γ-PGA was reduced to about 5 kDa.

It was reported that hydrolysis is not a suitable method to obtain cleaved polymers with a low polydispersity (Bioresource Technol. 2001; 79:207-225). The hydrolyzed γ-PGA with a high polydispersity may affect the coupling efficiency between γ-PGA and PLA and the size distribution of the prepared nanoparticles or micelles. To reduce the polydispersity of the hydrolyzed γ-PGA, the hydrolyzed γ-PGA (~5 kDa) was further dialyzed twice (using a membrane with MWCO: 3500 and a membrane with MWCO: 6000-8000) against distilled water. Thus obtained γ-PGA had a molecular weight of about 4 kDa with a polydispersity of about 1.3. This specific γ-PGA was used subsequently, together with PLA, to synthesize block copolymers to prepare the nanoparticles.

EXAMPLE NO. 4

Synthesis of γ-PGA-PLA Block Copolymers

Block copolymers composed of γ-PGA and PLA were synthesized using CDI to activate the terminal hydroxyl groups of PLA (Polymer 1997; 38:6235-6242). CDI (82 mg)

was dissolved in 1,4-dioxane (20 ml) in a nitrogen atmosphere and PLA (0.1 g) was subsequently added into the solution. The clear solution was stirred at 37° C. for 2 hours. Afterward, the solution was dialyzed extensively against distilled water at 4° C. Finally, the activated PLA was obtained via centrifugation.

The acidified form of the hydrolyzed γ-PGA (10 mg, Mn=4000, PDI=1.3) was dissolved in DMSO (5 ml) in a dry, stoppered 20 ml round bottom flask in a nitrogen atmosphere. After dissolution of DMAP (3 mg), a calculated amount of activated PLA (25 mg) was added. The solution was stirred at room temperature for 3 days, after which the reaction was stopped by adding 0.1 ml of concentrated HCl to neutralize DMAP and imidazole. The reaction mixture was transferred to a dialysis tube and dialyzed for 2 days against distilled water for several times at 4° C. Finally, the product (γ-PGA-PLA block copolymers) was lyophilized and stored at −20° C. until used.

Figure 1:
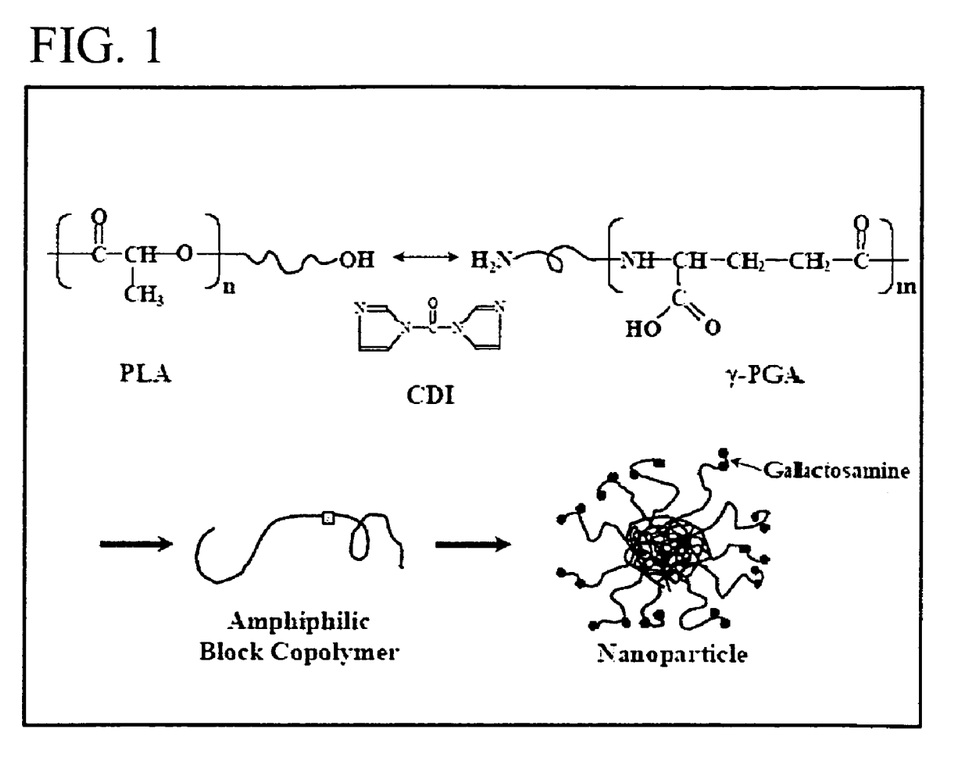
FIG. 1 shows schematic illustrations of synthesis of γ-PGA-PLA block copolymers and formation of self-assembled nanoparticles.
Figure 4:
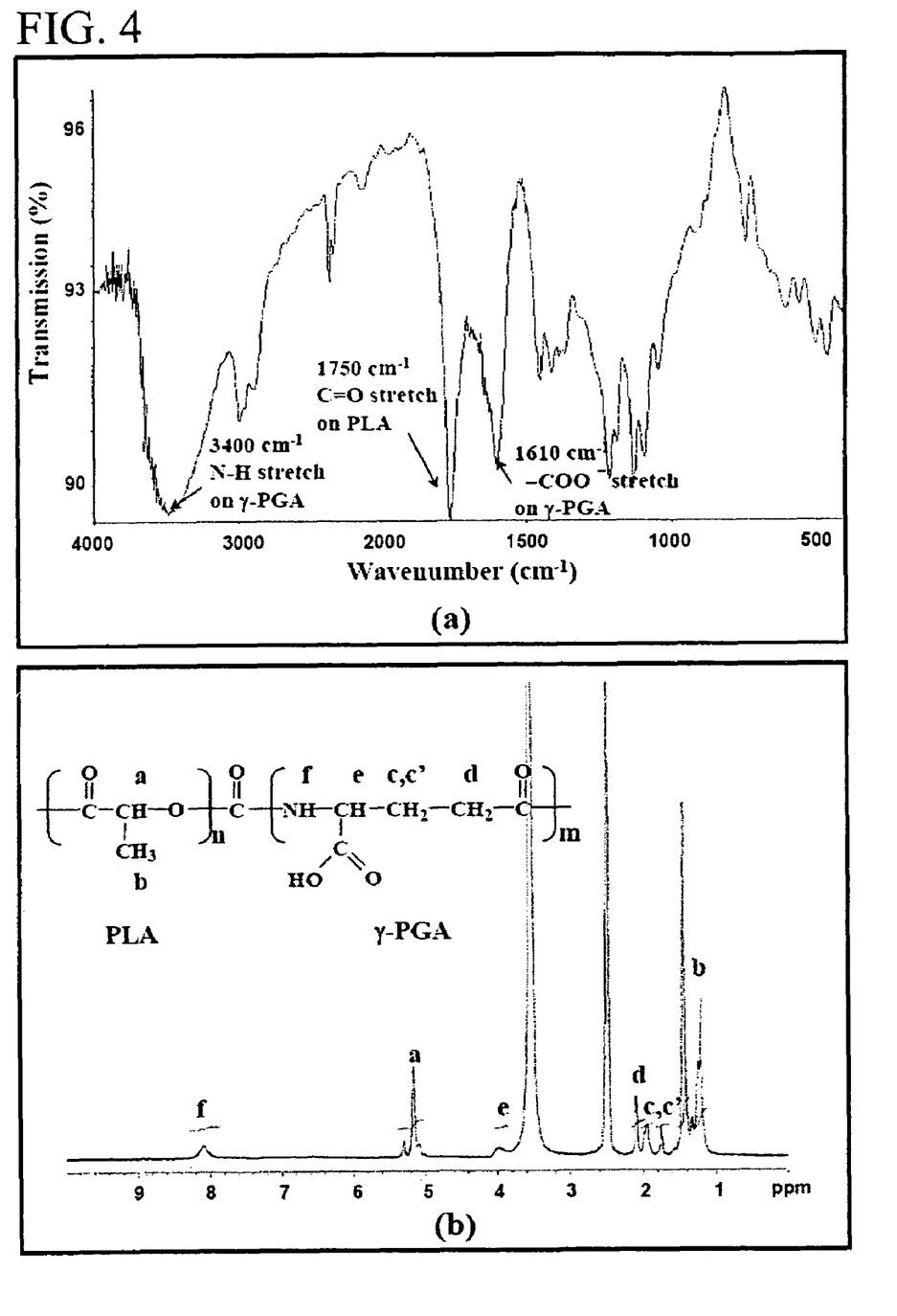
FIG. 4 shows (a) FT-IR and (b) $^1$H-NMR spectra of the synthesized γ-PGA-PLA block copolymer.

In the experiment CDI was used to activate the terminal hydroxyl group on PLA, which was then attached to the terminal amine group on γ-PGA to form amphiphilic block copolymers (FIG. 1). CDI has been commonly employed to activate the terminal hydroxyl group on PLA to produce an active derivative that may be attacked by nucleophiles (Anal. Biochem. 1983; 131:25-33). FIG. 4a and FIG. 4b show the FT-IR and $^1$H-NMR spectra of the synthesized γ-PGA-PLA block copolymers, respectively. In the FT-IR spectrum (FIG. 4a), the characteristic peak observed at 1750 $cm^{-1}$ was the C=O stretch on PLA and the characteristic peaks shown at 1610 and 3400 $cm^{-1}$ were the associated carboxylic acid salt (—$COO^-$ antisymmetric stretch) and the N—H stretch on γ-PGA, respectively. In the $^1$H-NMR spectrum (FIG. 4b), the chemical shifts at 1.42 and 5.20 ppm were the protons of methyl group (—$CH_3$) and methine (—CH) on PLA, respectively, while the main chemical shifts on γ-PGA described above were detected as well. The aforementioned results indicated that γ-PGA was successfully conjugated to PLA by CDI.

EXAMPLE NO. 5

Nanoparticle Preparation and Characterization

Nanoparticles were produced using the emulsion/solvent evaporation technique (Colloid. Surface. B, 2000; 18:301-313). Briefly, 10 mg of block copolymers were dissolved in 1 ml methylene chloride, then vortexed and emulsified in 10 ml of a 0.1 wt % sodium cholate solution using a sonicator (VCX-750, Sonics & Materials Inc., Newtown, Conn.) at cycles of 1 second sonication followed by 1 second of pauses, and total time 5 minutes. Afterward, the solvent was evaporated in a vacuum oven at 37° C. for 1 hour. The nanoparticles were then recovered by centrifugation for 20 minutes at 20000×g at 4° C. Subsequently, the nanoparticles were resuspended by phosphate buffered saline (PBS, pH 7.4, Sigma). The size distribution and zeta potential of nanoparticles were measured using a Zetasizer (3000HS, Malvern Instruments Ltd., Worcestershire, UK).

The transmission electron microscopy (TEM) and atomic force microscopy (AFM) were used to observe the morphology of nanoparticles. The TEM sample was prepared by placing a drop of the nanoparticle solution onto a 400 mesh copper grid coated with carbon. About 2 minutes after deposition, the grid was tapped with a filter paper to remove surface water and negatively stained by using a 2% (by w/v) phosphortungsten acid (PTA) solution. The AFM sample was prepared by casting a drop of the nanoparticle solution on a slide glass and then dried in vacuum.

During storage, aggregation of nanoparticles may occur and thus leads to lose their structural integrity or form precipitation of nanoparticles (Eur. J. Pharm. Sci. 1999; 8:99-107). Therefore, the stability of nanoparticles during storage must be evaluated. In the stability study, the prepared nanoparticles were suspended in PBS (1 mg/ml) at 4° C. and their particle size and zeta potential during storage were monitored by a Zetasizer.

Figure 5:
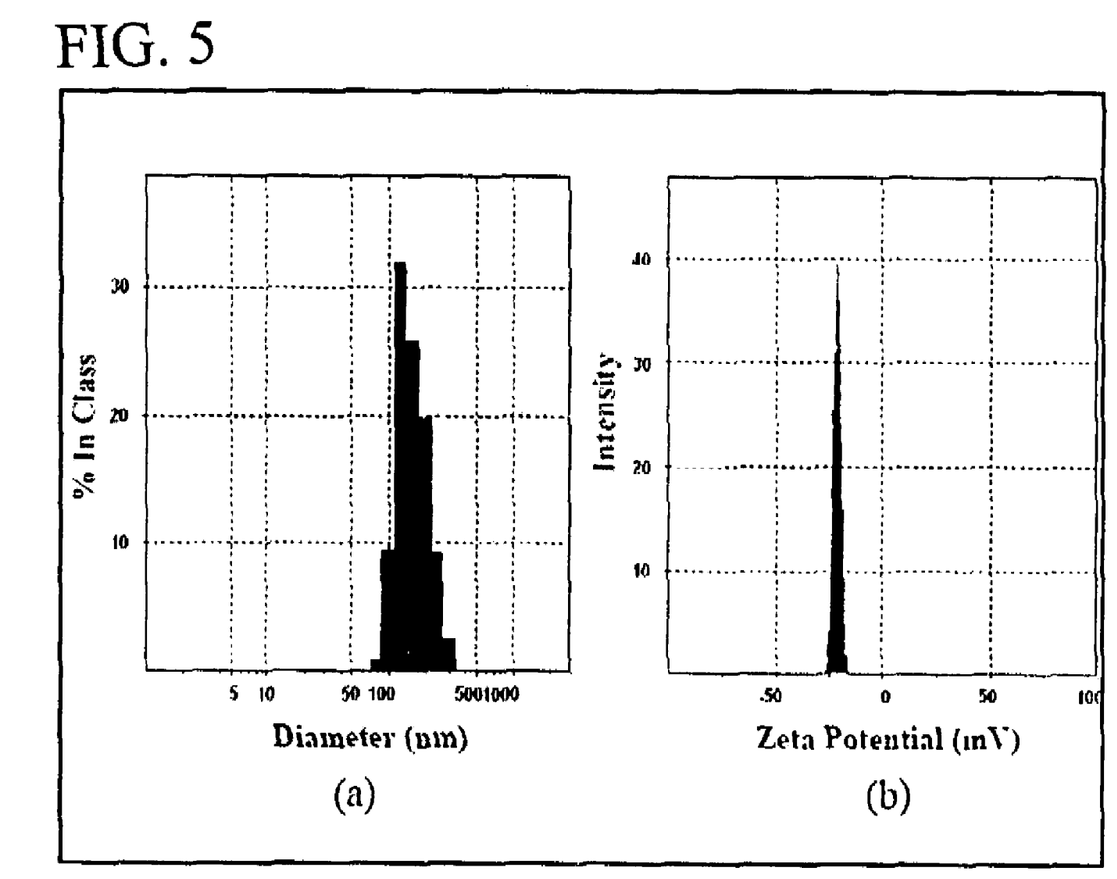
FIG. 5 shows (a) size distribution and (b) zeta potential of the prepared nanoparticles composed of γ-PGA-PLA block copolymers without galactosamine conjugated.

The size distribution and zeta potential of the nanoparticles without galactosamine conjugated in aqueous solution were investigated by dynamic light scattering. Size distribution and zeta potential may play important roles in determining the fate of nanoparticles after administration (Biomaterials 2004; 25:2843-2849). FIG. 5a and FIG. 5b show representative particle size and zeta potential distributions of the prepared nanoparticles. As shown, the prepared nanoparticles had a mean particle size of about 140 nm (FIG. 5a). Some aspects of the present invention provide a compound for treating liver cancers in a patient comprising a therapeutically effective amount of nanoparticles composed of γ-PGA-PLA block copolymers conjugated with galactosamine, wherein the mean particle size for nanoparticles is in the range of about 50 to 400 nm, preferably in the range of about 100 to 200 nm, and more preferably in the range of about 100 to 150 nm. Hashida et al. reported that the majority of the fenestrate of the liver sinusoid is usually smaller than 200 nm in diameter (J. Control. Release 1998; 53:301-310). Thus, large particles hardly reach the liver's parenchymal cells. Additionally, drug carriers with a diameter larger than 200 nm are readily scavenged non-specifically by monocytes and the reticuloendothelial system (Biochim. Biophys. Acta, 1994; 1190:99-107). It was reported that smaller particles tended to accumulate in the tumor sites due to the EPR (enhanced permeability and retention) effect (Crit. Rev. Ther. Drug Carrier Syst. 1989; 6:193-210) and a greater internalization was also observed (Adv. Drug Deliver. Rev. 2002; 54:695-713).

It was found that the prepared nanoparticles had a negative surface charge with a zeta potential of about −20 mV (FIG. 5b) due to the carboxyl (—$COO^-$) groups on the hydrophilic γ-PGA shell. This may affect the cellular uptake of the prepared nanoparticles due to electrostatic repulsion forces between the nanoparticles and the rather negatively charged surface of cells (Adv. Drug Deliver. Rev. 2002; 54:695-713). However, Li et al. reported that their conjugated paclitaxel onto α-PGA does not diminish the EPR effect and the accumulation and retention of α-PGA-paclitaxel in solid tumors (Adv. Drug Deliver. Rev. 2002; 54:695-713). They suggested that specific receptor-mediated interactions of α-PGA-drug conjugates containing targeting ligands may also increase the rate of polymer uptake into the target cells. Additionally, Hashida et al. suggested that the negatively charged carriers may be suitable for the selective delivery of drugs or pDNA to the liver's parenchymal cells, since the cationic nature of macromolecules and macromolecular drug conjugates may lead to non-specific binding to various cells after systemic administration (J. Control. Release 1998; 53:301-310).

Figure 6:
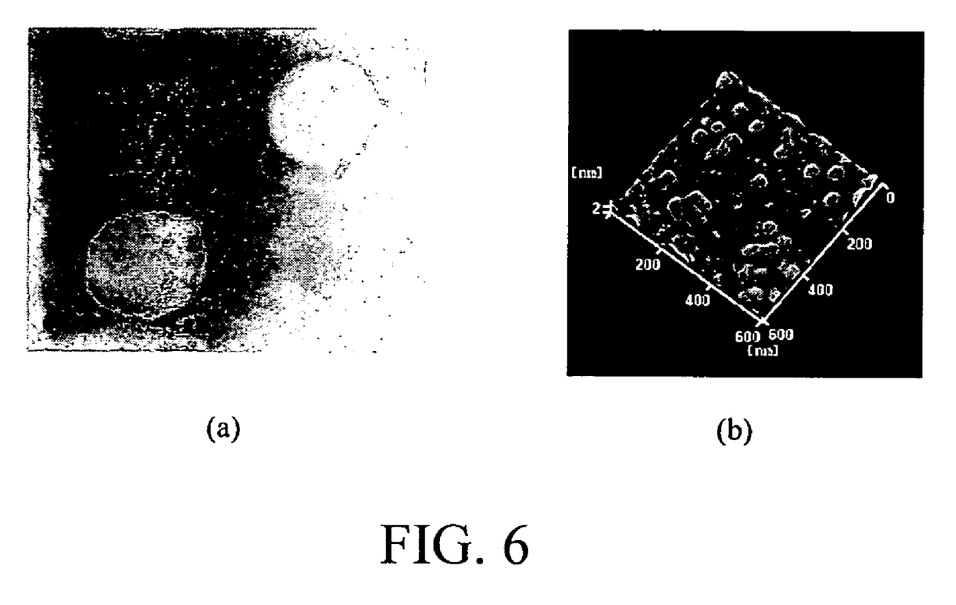
FIG. 6 shows morphology of the prepared nanoparticles composed of γ-PGA-PLA block copolymers: (a) TEM micrograph and (b) AFM micrograph.

The results obtained by the TEM and AFM examinations showed that the morphology of the prepared nanoparticles was spherical in shape with a smooth surface (FIG. 6). The diameters of nanoparticles observed by TEM and AFM were generally smaller than that obtained by dynamic light scattering. This is because the diameter of nanoparticles obtained by dynamic light scattering reflected the hydrodynamic diameter of nanoparticles swelled in aqueous solution, while those observed by TEM and AFM were the diameters of dried nanoparticles.

Figure 7:
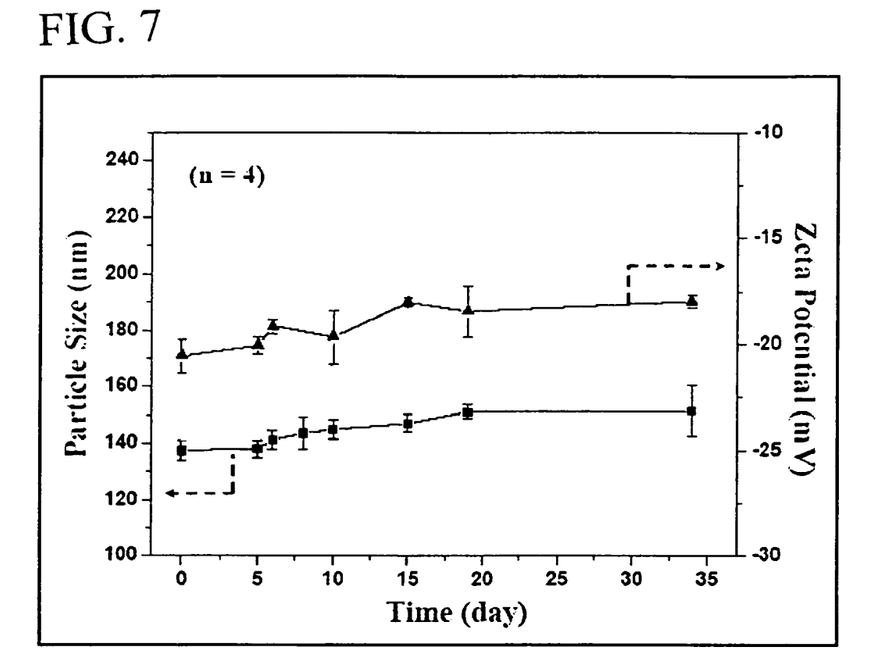
FIG. 7 shows changes in particle size (■, mean diameter) and zeta potential (▲) of the nanoparticles (1 mg/ml in PBS) during storage.

In the stability experiment, no aggregation or precipitation of nanoparticles was observed during storage for up to 1 month, as a result of the electrostatic repulsion between the negatively charged nanoparticles. Additionally, changes in particle size and zeta potential of the nanoparticles throughout the entire course of the study were minimal (FIG. 7). These results demonstrated that the prepared nanoparticles suspended in PBS were rather stable during storage.

EXAMPLE NO. 6

Fluorescence Spectroscopy (Pyrene)

The micellization of block copolymers in aqueous solutions depends on their concentration. Pyrene solubilization was used for the determination of the critical micelle concentration (CMC) in block copolymer solutions (Macromolecules 1995; 28:2303-2314). Stock solutions of pyrene ($6.0 \times 10^{-2}$M) were prepared in acetone and stored at 4° C. until used (J. Control. Release 2003; 90:363-374). For the measurement of steady-state fluorescence spectra, the stock pyrene solution was added to DI water to give a pyrene concentration of $12.0 \times 10^{-7}$M. Subsequently, the solution was placed in a vacuum oven at 60° C. for 1 hour to remove acetone from the solution. The acetone-free pyrene solution was mixed together with solutions of nanoparticles of which the concentration ranged from $5 \times 10^{-5}$ to 0.5 mg/ml. The final concentration of pyrene in each sample solution was $6.0 \times 10^{-7}$M, which is nearly equal to its solubility in water at room temperature. The emission wavelength at 395 nm was recorded on a spectrofluorometer (F-2500, Hitachi, Tokyo, Japan).

Figure 8:
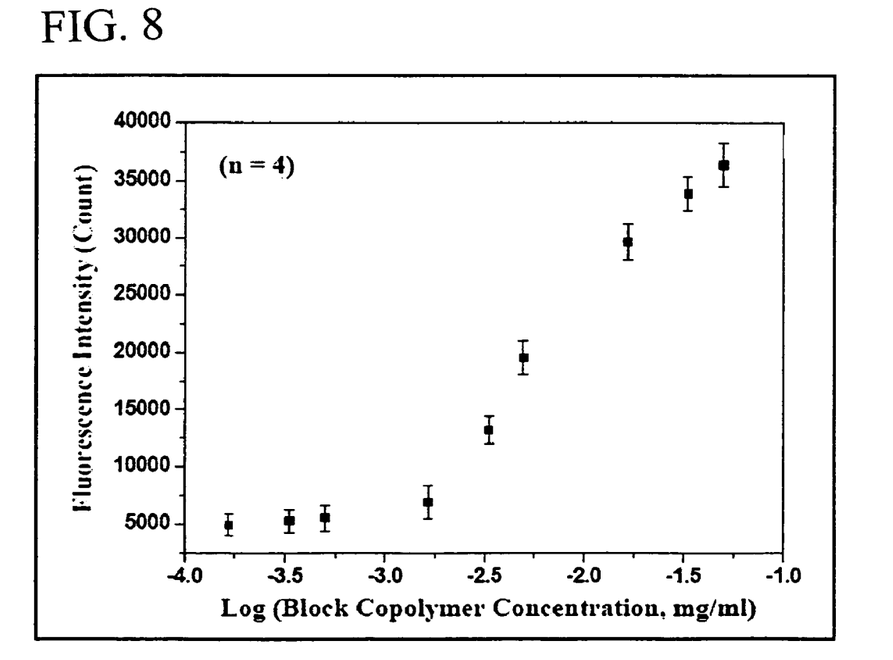
FIG. 8 shows plot of the fluorescence emission intensity of pyrene ($6.0 \times 10^{-7}$ M) versus the γ-PGA-PLA block copolymer concentration ($\lambda_{excitation}$=333 nm, $\lambda_{emission}$=395 nm).

To determine the critical micelle concentration (CMC) of nanoparticles in DI water, florescence measurements were carried out using pyrene as a probe (J. Control. Release 2003; 90:363-374). Pyrene is sensitive to changes in its environment, thus allows estimating the amounts of pyrene in nanoparticles at concentrations exceeding the CMC (Macromolecules 1995; 28:2303-2314). As shown in FIG. 8, the CMC of nanoparticles was about 2.3 µg/ml. The fluorescence intensity measured remained virtually constant below the CMC. Above the CMC, the fluorescence intensity increased substantially, indicating the incorporation of pyrene in the hydrophobic core of nanoparticles.

EXAMPLE NO. 7

Conjugation of Galactosamine to the Surface of Nanoparticles

Galactosamine (0, 2.5, or 10 mg/ml) was conjugated to the surface of nanoparticles (1 mg/ml) via an amide linkage by EDC in the presence of NHS (J. Biomed. Mat. Res. 2003; 64A:427-438; J. Appl. Polym. Sci. 2004; 91:4017-4026). The obtained nanoparticles were separated from unreacted molecules via ultrafiltration and then lyophilized. The amounts of galactosamine conjugated on nanoparticles were determined by the Morgan Elson assay (Bioconj. Chem. 2001; 12:890-899).

EXAMPLE NO. 8

Cell Uptake

In the examples, rhodamine-123 was used as a model hydrophobic fluorescent probe that can be encapsulated in the hydrophobic core in the preparation of nanoparticles with or without the conjugation of galactosamine for confocal laser scanning microscopy studies. Free rhodamine-123 was removed from the rhodamine-123-containing nanoparticle suspension via ultrafiltration. The rhodamine-123-containing nanoparticle suspension was then filtered through a 0.45 µm membrane for sterilization. Subsequently, 100 µl of rhodamine-123-containing nanoparticles (1 mg/ml) were added to HepG2 or human foreskin fibroblast (Hs68) cells, which were pre-cultured on a 35-mm glass dish for 24 hours. The experimental temperature was maintained at 37° C. by a temperature control system (DH-35 Culture Dish Heater, Warner Instruments Inc. Hamden, Conn.). After incubation for specific time intervals, the differential interference contrast (DIC) and fluorescence images were obtained real-time by using an inversed confocal laser scanning microscope (TCS SL, Leica, Germany). The fluorescence images were observed using an argon laser (excitation at 488 nm, emission collected at a range of 510-540 nm) and the quantitative analysis was performed using LCS Lite software (version 2.0).

Table 1 shows the mean particle size, zeta potential, and galactosamine content of the prepared nanoparticles with or without galactosamine conjugated. In the table, NPs represents the prepared nanoparticles without galactosamine conjugated. In the preparation of the nanoparticles conjugated with galactosamine, 2.5 or 10 mg/ml of galactosamine was added to 1 mg/ml of nanoparticles in the presence of EDC and NHS, thus obtained particles were termed Gal-NPs-2.5 and Gal-NPs-10, respectively, in the following discussion. It was found that the mean particle sizes of nanoparticles conjugated with galactosamine (Gal-NPs-2.5 and Gal-NPs-10) were similar to that without galactosamine conjugated (NPs, $p > 0.05$), while the values of their zeta potential decreased significantly ($p < 0.05$). This is because galactosamine was conjugated to the carboxyl ($—COO^-$) groups on γ-PGA and thus reduced the negative surface charge of the prepared nanoparticles (Gal-NPs-2.5 and Gal-NPs-10).

TABLE 1

Mean particle size, zeta potential, and galactosamine content of the prepared nanoparticles with or without galactosamine conjugated.

| Samples (n = 4) | Mean Particle Size (nm) | Zeta Potential (mV) | Galactosamine Content (nmol/mg nanoparticles) |
| --- | --- | --- | --- |
| NPs[&] | 140.6 ± 5.5 | −19.3 ± 3.4 | 0 |
| Gal-NPs-2.5* | 138.2 ± 6.7 | −15.4 ± 2.6 | 19.3 ± 2.5 |
| Gal-NPs-10* | 143.5 ± 4.2 | −11.2 ± 3.6 | 65.7 ± 3.6 |

[&]NPs: the prepared nanoparticles without galactosamine conjugated.
*Gal-NPs: the prepared nanoparticles with galactosamine conjugated.

Hepatocytes are known to recognize galactose- and N-acetylgalactosamine-terminated glycoproteins via the asialoglycoprotein (ASGP) receptors located on their surfaces (Int. J. Pharm. 1999; 188:39-47). Once a ligand binds to the ASGP receptor, the ligand-receptor complex is rapidly internalized by hepatocytes and the receptor recycles back to the surface of hepatocytes (Adv. Drug Deliver. Rev. 1989; 4:49-63). It was reported that the ASGP receptors are also abundantly expressed on the surfaces of various hepatoma cell lines (Adv. Drug Deliver. Rev. 1989; 4:49-63). To assess the extents of internalization of the prepared nanoparticles into HepG2 cells, NPs, Gal-NPs-2.5, and Gal-NPs-10 were labeled with rhodamine-123. Human foreskin fibroblast (Hs68) cells, which do not possess ASGP receptors, were used as a control cell line.

Figure 9A:
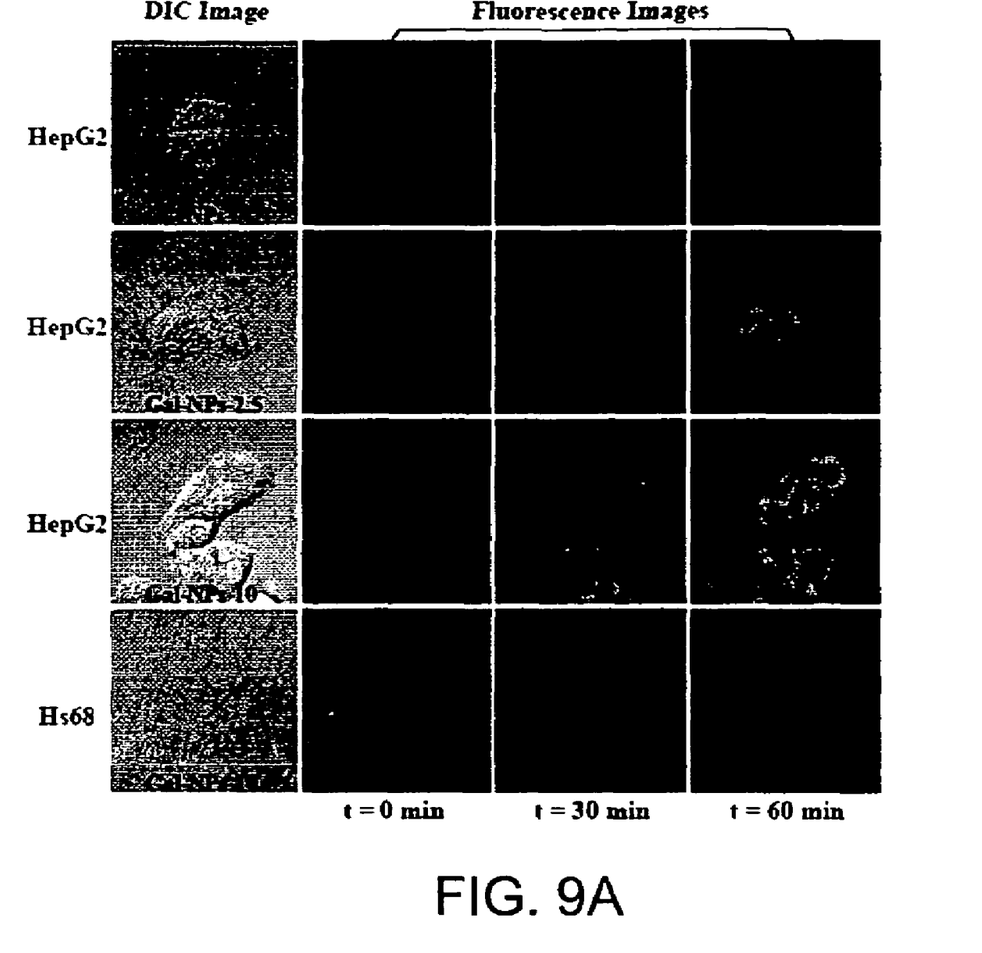
FIG. 9A shows differential interference contrast (DIC) and fluorescence images of HepG2 or Hs68 cells after incubating with the rhodamine-123-containing nanoparticles with or without galactosamine conjugated at 37° C. for distinct durations.
Figure 9B:
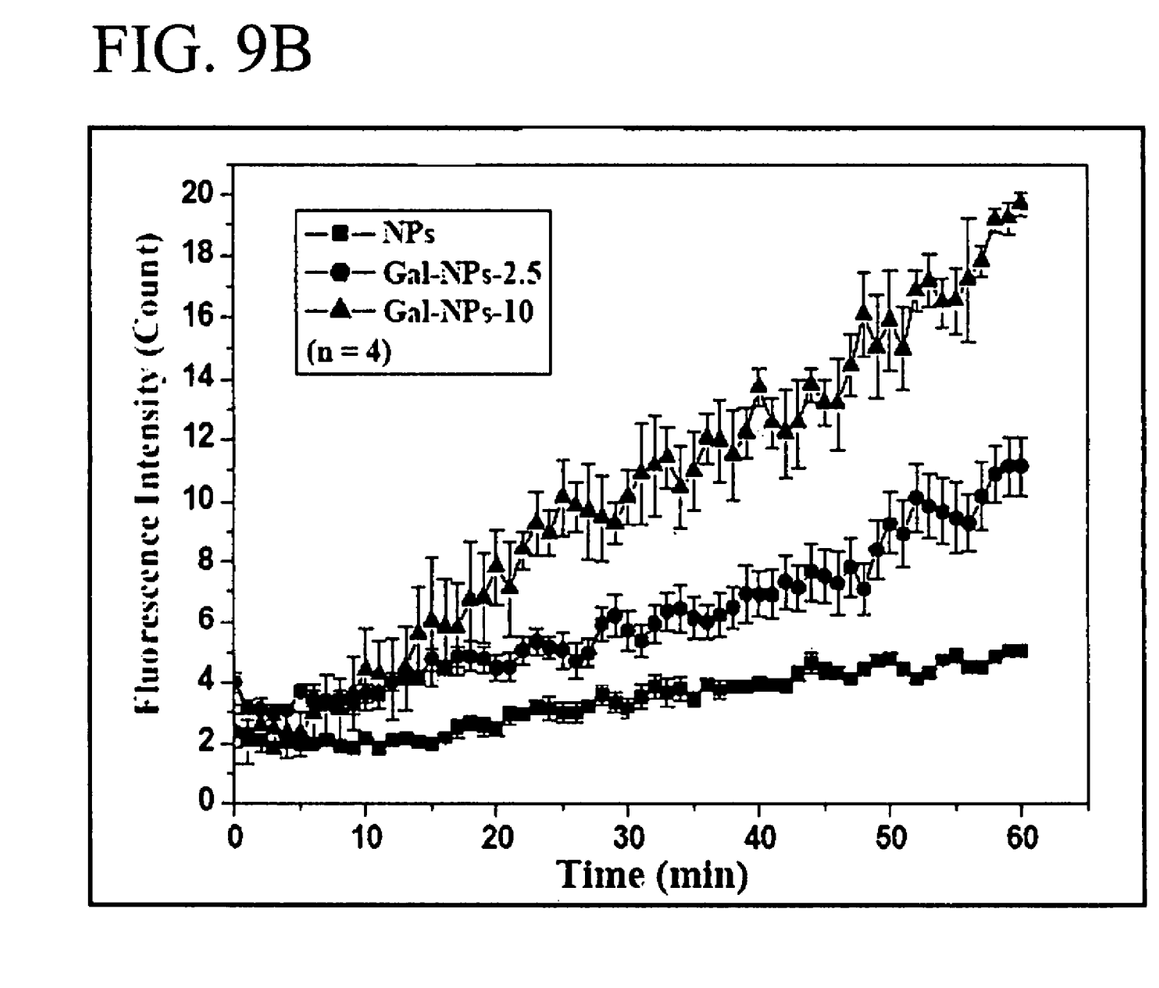
FIG. 9B shows the fluorescence intensity observed in HepG2 cells incubated with the rhodamine-123-containing nanoparticles with or without galactosamine conjugated at 37° C. for distinct durations.

Results of the differential interference contrast (DIC) and fluorescence images of HepG2 or Hs68 cells after incubating with rhodamine-123-containing nanoparticles with or without galactosamine conjugated at 37° C. for distinct durations are shown in FIG. 9A. The intensity of fluorescence observed in cells was analyzed using software (FIG. 9B). FIG. 9B shows the fluorescence intensity observed in HepG2 cells incubated with the rhodamine-123-containing nanoparticles with or without galactosamine conjugated at 37° C. for distinct durations. In FIGS. 9A and 9B, NPs are the prepared nanoparticles without galactosamine conjugated; and Gal-NPs are the prepared nanoparticles with galactosamine conjugated. As shown, in the incubation with NPs, little fluorescence was observed in HepG2 cells on the images taken at 30 and 60 minutes after incubation (FIGS. 9A and 9B). With increasing the galactosamine content conjugated on nanoparticles (Gal-NPs-2.5 and Gal-NPs-10), the intensity of fluorescence observed in HepG2 cells increased significantly ($p<0.05$). Additionally, the intensity of fluorescence observed in HepG2 cells incubated with the nanoparticles with or without galactosamine conjugated (NPs, Gal-NPs-2.5, or Gal-NPs-10) increased approximately linearly with increasing the duration of incubation (FIG. 9B). In contrast, there was no fluorescence observed in Hs68 cells (that is, without ASGP receptors) incubated with the nanoparticles with galactosamine conjugated. The aforementioned results indicated that the galactosylated nanoparticles prepared in the study had a specific interaction with HepG2 cells via ligand-receptor (ASGP) recognition.

EXAMPLE NO. 9

Cytotoxicity of Nanoparticles

Cytotoxicity of the prepared nanoparticles was evaluated in vitro using the MTT assay (J. Biomed Mater. Res. 2002; 61:360-369). The assay is based on mitochondrial dehydrogenase cell activity as an indicator of cell viability. Briefly, MTT [3-(4,5-dimethyl-thiazol-yl)-2,5-diphenyltetrazolium bromide, Sigma, St. Louis, Mo.] was dissolved in PBS with a concentration of 5 mg/ml as a stock MTT solution and filtered for sterilization. HepG2 cells were seeded in 24-well plates at $5\times10^4$ cells/well and were allowed to adhere overnight. The growth medium was replaced with a fresh one containing 0-100 μg/ml nanoparticles. The cells were then incubated for 48 hours and washed twice by 1 ml PBS. Subsequently, the cells were incubated in a growth medium containing 1 mg/ml MTT agent for an additional 4 hours at 37° C. and 500 μl of DMSO was added to each well to ensure solubilization of formazan crystals. Finally, the optical density readings were performed using a multiwell scanning spectrophotometer (MRX Microplate Reader, Dynatech Laboratories Inc., Chantilly, Va.) at a wavelength of 570 nm.

The effect of the prepared nanoparticles on cell viability was evaluated by the MTT assay. No significant cytotoxicity to HepG2 cells was observed for a particle concentration of up to 100 μg/ml. This indicated that the effect of cell viability on the cellular uptake of the prepared nanoparticles (with a particle concentration of 50 μg/ml) can be excluded in the studies.

Some aspects of the invention are related to the nanoparticles composed of γ-PGA-PLA block copolymers conjugated with galactosamine as a potential drug delivery system for treating liver cancers.

EXAMPLE NO. 10

Anticancer Drugs

Some aspects of the invention relate to a method of treating liver cancers in a patient comprising administering a therapeutically effective amount of nanoparticles composed of γ-PGA-PLA block copolymers conjugated with galactosamine, wherein the nanoparticles are loaded with at least one anticancer drug. Drugs such as doxorubicin, adriamycin, cisplatin, taxol, and 5-fluorouracil are being widely used in chemotherapies for the treatment of cancer. In the aforementioned Example no. 5, nanoparticles were produced using the emulsion/solvent evaporation technique by mixing effective amounts of raw material (namely γ-PGA, PLA, and at least one selected anticancer drug), followed by conjugation with galactosamine.

Nanoparticle preparations, mainly used for intravenous injection, are employed for targeting hepatoma cells or other solid tumors. When nanoparticle or micelle preparations of anticancer drugs of the present invention are administered, the size of particles ranging from tens to hundreds of nanometers let them penetrate into tumor tissues across the wall of blood vessel which have loosened cell contact and have specific affinity to cancer cells.

U.S. Pat. No. 6,752,981, the entire contents of which are incorporated herein by reference, discloses preferred classes of anticancer drugs including: epipodophyllotoxins, camptothecins, endiyne antibiotics, taxanes, coformycins, anthracycline glycosides, mytomycin, combretastatin, anthrapyrazoles, and polyamine biosynthesis inhibitors.

Preferred epipodophyllotoxins include Etoposide, Teniposide, NK-611, GL-331, and azatoxin. Preferred camptothecins include Camptothecin, Topotecan, Irinotecan (CPT-11), Lurtotecan (GI 147211), 9-aminocamptothecin, GG-211, DX-8951F, SKF 107874, and SKF 108025. Preferred taxanes include paclitaxel, docetaxel, and FCE-28161. Preferred combretastatins include combretastatin A-4 and the reported (S,S) dioxolane analog (Bioorg. Med. Chem. Lett. 88: 1997-2000 (1998). Preferred anthrapyrazoles include mitoxantrone, piroxantrone, and Losoxantrone. Preferred Anthracyclines include Doxorubicin, Daunorubicin, Idarubicin, Pirarubicin, and Epirubicin. Preferred Enediyne Antibiotics include neocarzinostatin, calicheamicin, and esperamicin. In another aspect, Mitomycin is also preferred. Preferred Polyamine Biosynthesis Inhibitors include eflornithine.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A pharmaceutical composition of nanoparticles for treating liver cancer in a patient, said nanoparticles comprising γ-PGA-PLA block copolymers that are conjugated with galactosamine.

2. The pharmaceutical composition of claim 1, wherein a therapeutically effective amount of said nanoparticles for treating the liver cancer has a average particulate concentration of nanoparticles of 50 μg/ml in a solution.

3. The pharmaceutical composition of claim 1, wherein γ-PGA prior to forming the γ-PGA-PLA block copolymers has a molecular weight of about 4 kDa and a polydispersity index of about 1.3.

4. The pharmaceutical composition of claim 1, wherein a mean particle size of nanoparticles in a solution is in the range of about 50 to 400 nm.

5. The parmaceutical composition of claim 1, wherein a mean particle size of nanoparticles in a solution is in the range of about 100 to 200 nm.

6. The pharmaceutical composition of claim 1, wherein a mean particle size of nanoparticles in a solution is in the range of about 100 to 150 nm.

7. The pharmaceutical composition of claim 1, wherein at least a portion of the nanoparticles is loaded with at least one anticancer drug.

8. The pharmaceutical composition of claim 1, wherein the nanoparticles are loaded with 5-fluorouracil.

9. The pharmaceutical composition of claim 1, wherein the nanoparticles are loaded with pharmaceutically active epipodophyllotoxins.

10. The pharmaceutical composition of claim 1, wherein at least a portion of the nanoparticles comprises a hydrophobic inner core.

11. The pharmaceutical composition of claim 1, wherein at least a portion of the nanoparticles comprises a hydrophilic outer shell.

12. The pharmaceutical composition of claim 1, wherein said nanoparticles have a negative surface charge.

13. The pharmaceutical composition of claim 1, wherein said nanoparticles have a surface zeta potential of about −20 mV or higher.

14. The pharmaceutical composition of claim 1, wherein said nanoparticles are adapted for delivery to a blood vessel of the patient for treating the liver cancer.

15. The pharmaceutical composition of claim 1, wherein said nanoparticles are adapted for intravenous injection for treating the liver cancer in the patient.

16. The pharmaceutical composition of claim 1, wherein at least a portion of the nanoparticles comprises a hydrophobic outer shell.

17. The pharmaceutical composition of claim 1, wherein the γ-PGA-PLA block copolymers are synthesized via a simple coupling reaction process between γ-PGA polymers and PLA polymers.

18. The pharmaceutical composition of claim 7, wherein said at least one anticancer drug is paclitaxel.

* * * * *